United States Patent [19]
Lai et al.

[11] Patent Number: 5,807,742
[45] Date of Patent: *Sep. 15, 1998

[54] NEUROKININ RECEPTOR CELL LINES

[75] Inventors: Josephine Yuen-Wai Lai; Alden Keith Henderson, both of Tucson, Ariz.; Stephen Henderson Buck, Cincinnati, Ohio; William R. Roeske; Henry J. Yamamura, both of Tucson, Ariz.; Shigetada Nakanishi, Kyoto, Japan

[73] Assignee: Merrell Pharmaceuticals Inc., Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 692,287

[22] Filed: Aug. 1, 1996

Related U.S. Application Data

[63] Continuation of Ser. No. 546,519, Oct. 30, 1995, abandoned, which is a continuation of Ser. No. 321,081, Oct. 11, 1994, abandoned, which is a continuation of Ser. No. 184,761, Jan. 19, 1994, abandoned, which is a continuation of Ser. No. 82,827, Jun. 25, 1993, abandoned, which is a continuation of Ser. No. 883,242, May 7, 1992, abandoned, which is a continuation of Ser. No. 518,683, May 3, 1990, abandoned.

[51] Int. Cl.$^6$ .................................................. C12N 5/06
[52] U.S. Cl. ..................... 435/357; 435/320.1; 435/69.1; 435/172.3; 435/354; 435/356; 536/23.51; 935/66; 935/9; 935/70
[58] Field of Search ................................ 435/172.3, 69.1; 536/23.51

[56] References Cited

PUBLICATIONS

Giersbergen, P., et al., Characterization of a Tachykinin Peptide NK$_2$ Receptor Transfected Into Murine Fibroblast B82 Cells, PNAS 88, 1661–1665 (1991),.

Letter of Brobbie A. Brandon, Head of the ATCC Patent Depository, dated May 17, 1991.

Henderson, A.K., et al., The Cloned Neurokinin A Receptor Mediates Polyphosphinositide Hydrolysis in Transfected Murine Fibroblasts, FASEB J. 4(3)A315; abstract #288 (1990).

Gunning, P., et al., A Human β–Actin Expression Vector System Directs High–Level Accumulation of Antisense Transcripts, PNAS 84, 4831–4835 (1987).

Masu, Y., et al., cDNA Cloning of Bovine Substance–K Receptor Through Oocyte Expression System, Nature 329, 836–838 (1987).

Couture, R., et al., Characterization of the Peripheral Action of Neurokinins and Neurokinin Receptor Selective Agonist On the Rat Cardiovascular System, Archives of Pharmacology 340, 547–557 (1989).

Hashimoto, T. et al., Synthesis of Neurokinin B Analogs and Their Activities As Agonist and Antagonists, Chem. Phar. Bull. 35(8), 3442–3446 (1987).

Yokota, Y., et al., Molecular Characterization of a Functional cDNA for Rat Substance P Receptor, JBC 264(30), 17649–17652 (1989).

Henderson et al abstract FASEB J 4(3) A315. 1990.

Gunning et al PNAS 84:4831. 1987.

Masu et al Nature 329:836. 1987.

Couture et al NS Arch. Pharmacal 340:547. 1987.

Mashimoto et al Chem. Phar. bull. 35(8):3442. 1987.

*Primary Examiner*—Christopher S.F. Low
*Attorney, Agent, or Firm*—T. Helen Payne

[57] ABSTRACT

A method for producing high level expression of neuropeptide receptors and stable cell lines useful therein. This method involves culturing a cell line containing amplified copies of a cDNA sequence encoding a neuropeptide receptor containing an expression control sequence taken from the β-actin transcriptional control element.

13 Claims, 5 Drawing Sheets

FIG.1

| CELL LINE | SPECIFIC BINDING *<br>DPM/μg PROTEIN | % SPECIFIC |
|---|---|---|
| B82 (STANDARD CELL LINE) | 138 | 13 |
| LK4V (VECTOR CONTROL) | 16 | 37 |
| LK3-3 (MUSCARINIC CONTROL) | 1 | 0 |
| SKLKB82 #3 | 265 | 90 |
| #6 | 11 | 59 |
| #7 | 268 | 95 |
| #8 | 26 | 69 |
| #11 | 9 | 52 |
| #12 | 51 | 83 |
| #13 | 221 | 94 |
| #13 | 176 | 94 |
| #14 | 54 | 82 |
| #15 | 107 | 88 |
| #17 | 19 | 68 |
| #18 | 21 | 62 |

\* USING 0.5 nM [$^{125}$I] NKA

FIG.4

| | SKLKB82 #3 CELLS | HAMSTER URINARY BLADDER |
|---|---|---|
| NKA | 0.3 ± 0.1 | 0.2 ± 0.04 |
| Nle$^{10}$ NKA(4-10) | 14 ± 7 | 9 ± 1 |
| SP | 85 ± 21 | 175 ± 25 |
| Senktide | > 10,000 | > 10,000 |

*MEAN ± S.E.M. OF THREE DETERMINATIONS. SKLKB82 # 3 CELLS AND HUB MEMBRANES ASSAYED IN PARALLEL IN EACH DETERMINATION. 0.1 nM LIGAND USED IN EACH EXPERIMENT.

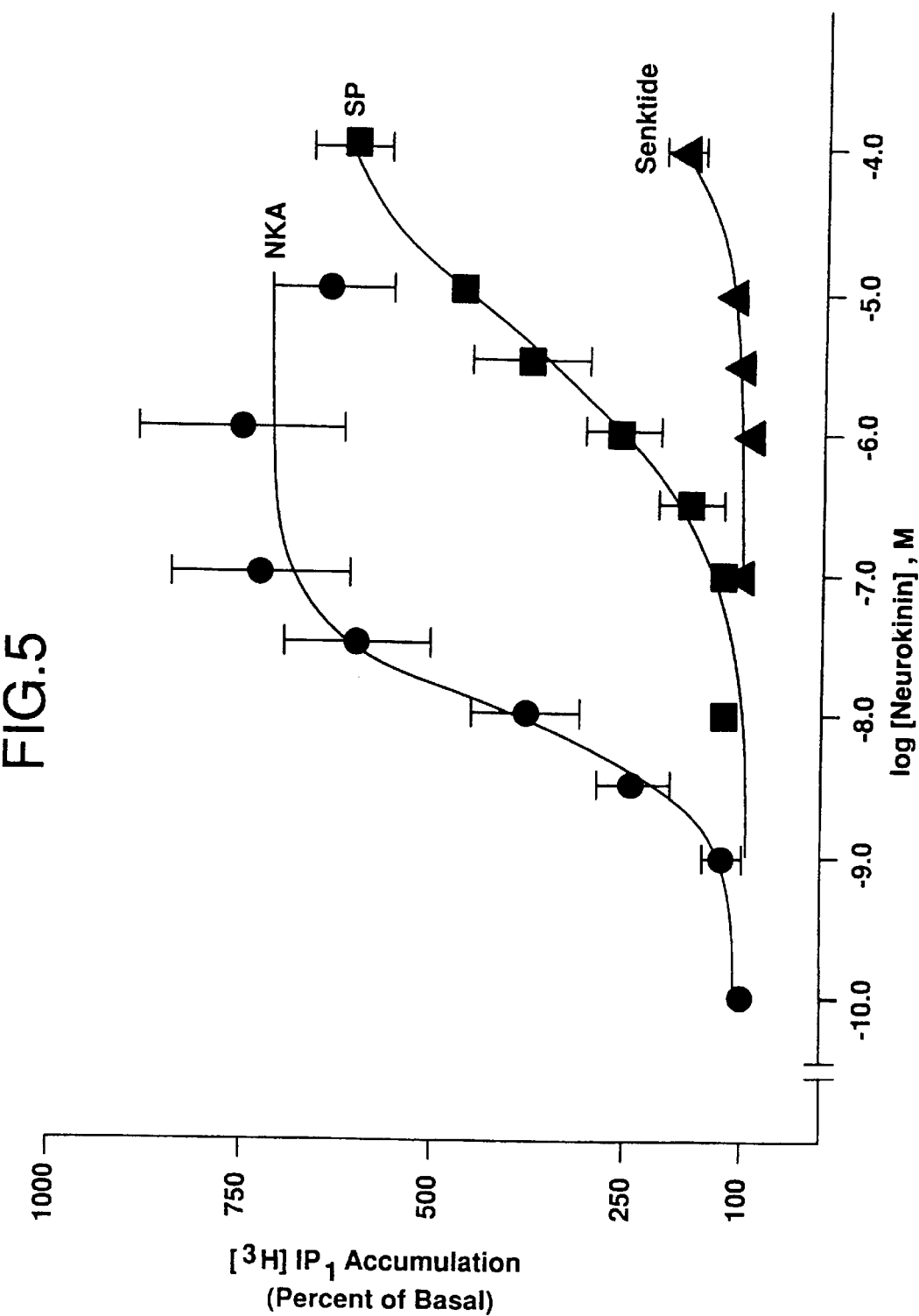

NEUROKININ RECEPTOR CELL LINES

This is a continuation of application Ser. No. 08/546,519, filed Oct. 30, 1995; now abandoned which is a continuation of application Ser. No. 08/321,081 filed Oct. 11, 1994, now abandoned; which is a continuation of application Ser. No. 08/184,761, Filed Jan. 19, 1994, now abandoned; which is a continuation of application Ser. No. 08/082,827, filed Jun. 25, 1993, now abandoned; which is a continuation of application Ser. No. 07/883,242, filed May 7, 1992, now abandoned; which is a continuation of application Ser. No. 07/518,683, filed May 3, 1990, now abandoned, which is herein incorporated by reference.

This invention relates to a novel genetically engineered mammalian cell line which is capable of high level expression of neurokinin A receptors.

BACKGROUND OF THE INVENTION

Our knowledge of the origin of neurotransmitter receptor subtypes has been advanced by the identification of several neurotransmitter genes and the pharmacological characterization of the gene products, which are generally present in nature in very limited quantities. Within the peptide neurotransmitter family are the tachykinins. Mammals contain three distinct tachykinin neuropeptides, substance P, neurokinin A (also designated NKA and known as substance K), and neurokinin B (also known as neuromedin K), and it has been suggested that there are multiple tachykinin receptor subtypes. Expression of the recombinant receptor protein therefore is an important goal in the characterization of the neuropeptide receptors and in understanding their function and pharmacological significance.

This invention relates generally to a expression system for obtaining high level expression of selected neuropeptide receptors. More specifically, the invention discloses the host cells B82 which express high levels of neurokinin A receptors as effected by a cDNA encoding the bovine neurokinin A receptor, which has been operatively linked to the human β-actin transcriptional control element.

SUMMARY OF THE INVENTION

The invention describes a new cell line that has been established from transfection of the mouse fibroblast cell line B82 with an expression plasmid containing the neurokinin A receptor gene. The new cell line is capable of expression of high levels of neurokinin A receptors defined by the binding of neurokinin A. The selectable marker chosen for the cloning of transfected B82 cells in this case was the aminoglycoside phosphotransferase (APH) gene.

BRIEF DESCRIPTION OF THE DRAWINGS

FIG. 1 The amount of receptor binding of [$^{125}$I]-NKA was evaluated in three types of control cell lines and in twelve lines that had been transfected with pSKR56S cDNA in the pHβAPr-1-neo-SKR vector. There was little or not specific binding in any of the controls (standard B82 line; LK4V line transfected with vector alone; LK3-3 line containing the transfected muscarinic M1 receptor (Lai et al., Life Sciences 42: 2489, 1988). Among the NKA receptor transfected lines, there were low, medium, and high binding levels observed. All of the transfected cell lines exhibited higher proportional specific binding than the three control cell lines.

FIG. 4 Comparison of competition $K_I$ values for various tachykinin related pepties on [$^{125}$I]NKA receptor binding in transfected SKLKB82#3 cells and hamster unrinary bladder. In both tissues NKA was the most potent inhibitor of binding, followed by Nle$^{10}$NKA (4–10), substance P, and senktide. This potency rank-order is that of a NKA receptor of the $NK_2$ type. Since the rank-order was similar in both tissues, this indicates that the cell lines transfected with the pSKR56S cDNA contain an authentic neurokinin A receptor.

FIG. 5 The SKLKB82#3 cells exhibited a doese respon in [$^3$H]IP$_1$ accumulation toward NKA (●), substance P (■), and senktide (▲). The EC50s are 10 nM for NKA, 4.8 μM for SP, and 1.3 mM (estimated) for senktide. Data points are arithmetic mean ±S.E.M. of three separate experiments done in duplicate.

DETAILED DESCRIPTION OF THE INVENTION

Definitions

Figure 2:
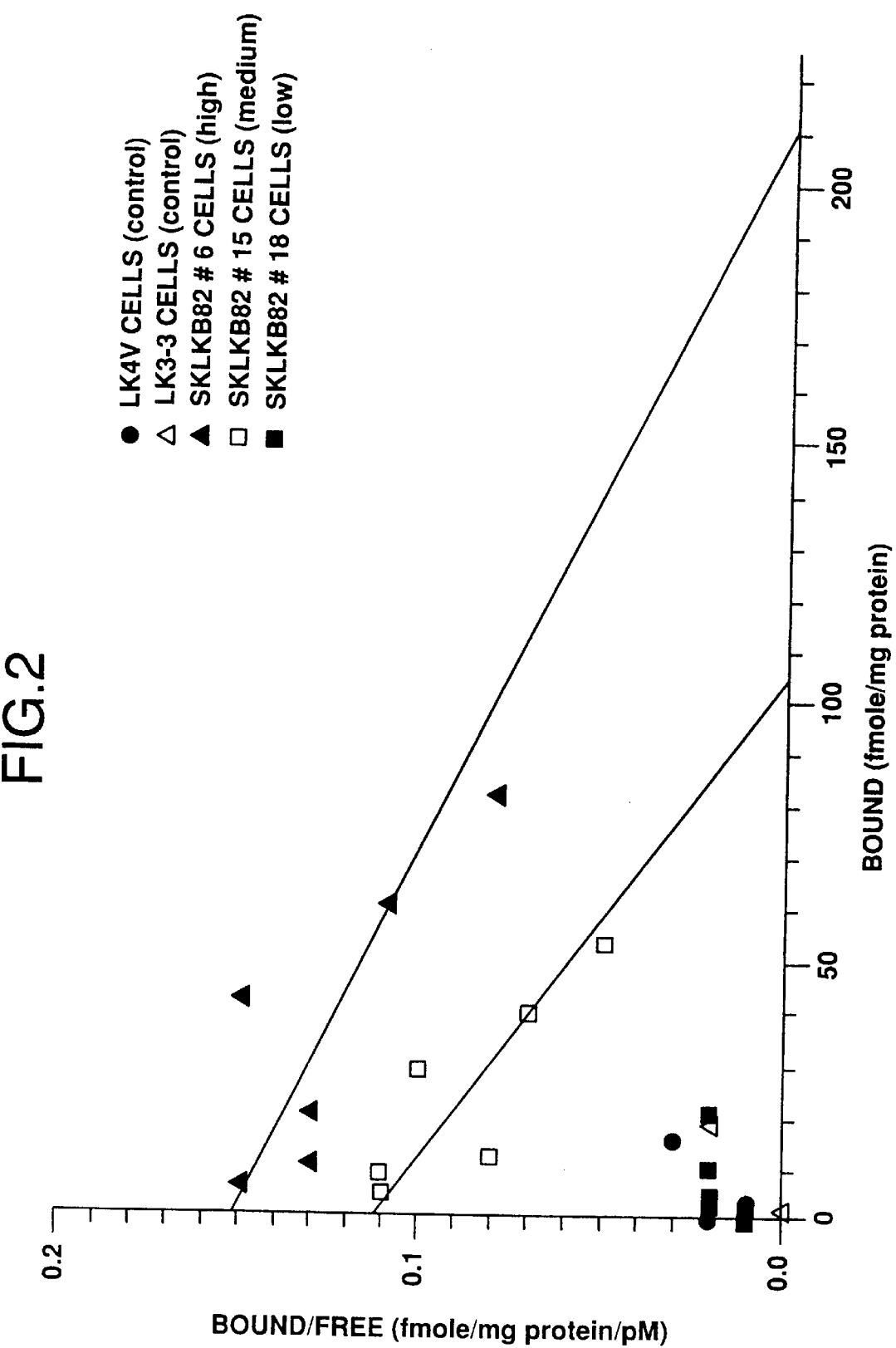
FIG. 2 Scatchard analysis of [$^{125}$I]NKA saturation binding experiments in two control cell lines and in three cell lines transfected with the NKA receptor cDNA. Little or no detectable binding was observed in the control lines or in the low receptor level line (SKLKB82#15). Substantial levels of receptor binding were observed in the medium level (SKLKB82#18) and in the high level (#SKLKB82#6) cell lines. $K_D$ values were 1.4 nM for SKLKB82#6 and 0.9 nM for SKLKB82#15 (X-intercept=$B_{MAX}$; negative inverse of slope=$K_D$).

Several terms are set forth in the invention. Those terms are meant to have the following meanings.

Amplifying cells: Amplifying cells comprises culturing a cell line containing a selectable marker with a selective agent that gives rise to a population of cells that have an increased level expression of a desired protein. Generally, the result of amplification is an increased copy number of a plasmid present either extracellularly or one that has integrated into the genomic DNA. Selectable markers chosen include the genes for adenosine deaminase(ADA), aminoglycoside phosphotransferase (neo, G418, APH), dihydrofolate reductase (DFR), hygromycin-B-phosphotransferase(HPH), thymidine kinase (TK), and xanthine-guanine phosphoribosyltransferase (XGPRT, gpt).

Biologically active receptors: A function or set of functions performed by a receptor in a biological context, that may either be in vivo in an organism or in in vitro in a biochemical system. Biologically active receptors may be divided into catalytic and effector activities.

Catalytic activities: Catalytic activities of receptors generally involve the activation and/or suppression of cellular factors and pathways through the binding of the ligand.

Complementary DNA or cDNA: A DNA molecule or sequence which has been enzymatically synthesized from the sequences present in a mRNA template.

DNA or Plasmid Construct: A DNA sequence or plasmid containing such sequence which may be isolated in whole or partial form which has been modified to contain segments of DNA which are combined and juxtaposed in a manner which would otherwise not exist in nature.

Effector activities: Effector activities of receptors include specific binding of the biological ligand. Effector activity frequently augments, or is essential to a catalytic activity under physiological conditions.

Expression: Expression is the use of the sequences from the transfection of the plasmid or vector that is transcribed into mRNA which then is utilize to direct the synthesis of protein in conjunction with the cellular machinery of the host organism.

Genetic Code: The sequence of nucleotides in a gene that determines the order of amino acids in a corresponding protein. The genetic code is the relationship between the twenty-letter language of amino acids used in proteins to the four letter language of the nucleic acids. The genetic code is degenerate in that more than one codon can specify the same amino acid. However, all codons are unambiguous in that each specifies no more than one amino acid or signal termination of translation of the peptide or protein.

Hybridizing: The process of forming a double-stranded molecule by complementary base-paring between two single-stranded DNA molecules, or a single-stranded DNA molecule and an RNA molecule. As such plasmid, vectors, or portions thereof, or DNA derived from pieces of synthetic synthesized regions can be used to detect a complementary base-pairing sequence that has a complementary or homologous sequence, often referred to as a probe. The probe is invariably labeled with a radioactive, fluoresing, or biotin derivative so as to allow autoradiographic or enzymatic detection of the hybridization reaction.

Joined: DNA sequences are said to be joined when the 5' and 3' ends of one DNA sequence are attached, by phosphodiester bonds, to the 3' and 5' ends, respectively, of an adjacent DNA sequence. Joining may be achieved by such methods as enzymatic ligation of blunt or cohesive termini, by synthesis of joined sequences through cDNA cloning, or by deletion, insertion, or change of internal sequences by a process of directed mutagenesis.

Mutagenesis: The process whereby DNA sequences are altered. Such changes in the DNA sequence may be employed to bring about an alteration in the functional activity of the sequence or affect the nature of protein sequence that may be encoded within the sequence. Amongst the numerous techniques employed to bring about changes in DNA sequences are the use of synthetic oligonucleotides to direct the desired change. Such changes may insert, delete, or change the surrounding nucleotide sequences. One may also change DNA sequences using chemical mutagens or by placing the cells in which the DNA resides under selective environmental pressures so as to effect a change in the DNA.

Non-biologically active receptors: Receptors that may be defective in either their catalytic or effector activities, or both. Receptors of this type would be able to be produced through mutagenesis of the receptor sequence.

Operative association: A transcriptional control sequence is in operative association when when a promoter and its associated regulatory elements are so joined to a gene that it operates to transcribe said gene.

Plasmid or Vector: A DNA construct containing genetic information which may provide for its replication when inserted into a host cell. A plasmid generally contains at least one gene sequence to be expressed in the host cell, as well as sequences which facilitate such expression, including promoters and transcription initiation sites. It may be a linear or a closed circular molecule.

Selection: Any means of identifying a clone that contains a desired recombinant DNA molecule. Such means of identification may include a selectable marker whereby the gene carried by a vector that confers a recognizable characteristic to a cell containing the vector.

Transcriptional control sequences: Those DNA sequence elements that provide for transcription and termination of aligned genes by RNA polymerase II. The DNA sequences involved for RNA polymerase II recognition, initiation, and termination are not meant as a limit upon the presence of other sequences. The transcription control sequence may also include sequences and associated transcription factors that would enable an operational transcription unit. Addition of enhancers, tissue specific regulatory elements, and maintence factors all fall within the scope of transcriptional control sequences. Furthermore, such sequences need not be juxtaposed to the transcription initiation and termination sequences and thereby may be positioned 5' or 3' to these sequences, including those inserted in intervening sequences and serves therein as a part of the transcriptional unit.

Transfection: Is the introduction of DNA into cultured cells generally for the purpose of acquiring new genes in a cell.

Description and Maintenance of Cell Lines:

The B82 cell line is a mouse L cell line which is a heteroploid fibroblast-like cell that is thymidine kinase deficient and is selectable with 5-bromodeoxyuridine.

Construction of Neurokinin A Receptor Expression Vectors

Clones for the neurokinin A receptor were isolated from a cDNA library from bovine stomach mRNA (Masu et. al., Nature 329, 836–838). The bovine cDNA library was constructed in a lamda expression vector containing the SP6 and T7 promoters to provide a mechanism to transcribe inserted heterologous genes *in vitro*. mRNAs were expressed in functional form following microinjection of the mRNA in frog oocytes, previously shown to have the cellular machinery to express the exogenous receptor mRNA. A cDNA clone for the bovine neurokinin A (NKA) receptor was isolated using electrophysiological measurements of the injected Xenopus oocytes. Individual clones expressing neurokinin A receptors were able to be found by electrophysiological changes of the oocytes capable of responding to neurokinin A through the NKA receptor.

Several NKA receptor cDNA clones were found in this manner and their structures determined. The clone pSKR56S was chosen for expression in the instant invention. The cDNA insert of this clone was initially subcloned into the cloning vector pGEM3 and was used as the source of DNA for cloning into the expression vector pHβAPr-1-neo. All reconstructions of the vector and subcloning were done in *E. Coli* strains and are within the scope of someone skilled in the art.

Expression of the bovine neurokinin A gene utilized the elements present in the expression vector pHβAPr-1-neo (Gunning, et al., PNAS 84,4831–4835). The essential elements of the vector consist of the 5' flanking sequence of the human β-actin promoter and the first intervening sequence (IVS1) linked to unique restriction sites for insertion of exogenous genes, and a simian virus 40 (SV40) polyadenylation signal. The restriction sites 3' to the promoter for insertion of exogenous genes are derived from the multiple cloning region of pSP64. The expression elements from SV40 of pHβAPr-1-neo were derived from the framework of the Okayama-Berg expression vector pcDV1 and used in the creation of the parent vector pHβAPr-1. pHβAPr-1-neo was a subsequent modification of pHβAPr-1 to incorporate the neomycin-resistance gene (directed by the SV40 early promoter) to allow for selection of cells that stably integrate exogenous DNA. The neomycin gene and SV40 promoter were taken from the plasmid pSV2neo as a EcoRI/ PvuII DNA fragment and inserted between the EcoRI and ClaI sites of pHβAPr-1 to create pHβAPr-1-neo.

pHβAPr-1-neo-SKR is the instant vector for expression of the neurokinin A receptor. Cloning of the NKA receptor gene into pHβAPr-1-neo was accomplished by moving the HindIII-BamHI fragment in pGEM3, which includes the NKA receptor gene derived from pSKR56S, and joining it to the parent expression vector pHβAPr-1-neo.

Vector and DNA

The procedures for plasmid construction and DNA preparation are well known in the art and have been produced by a number of authorities (Maniantis, et al, Molecular Cloning (1982); Ausubel, et al. Current Protocols in Molecular Biology). All plasmids were grown in the *Escherichia coli* host HB101 or TG1. The plasmids have all been described.

The vectors for use in producing the cells or cell lines useful in the method of the present invention are preferably supercoiled, double-stranded circular constructs. All enzymes are commercially available and are utilized using procedures well known to those trained in the art, and are well described in the literature and by the commercial suppliers. Nucleotide sequencing was performed using the dideoxy chain-termination method or can be performed by other well known standard techniques in the art.

Transfection of Mammalian Cell Lines

Generally three techniques are currently used for introduction of DNA into mammalian cells: calcium phosphate transfection, DEAE-dextran transfection, and electroporation. The first two procedures produce a chemical environment that results in the DNA attaching to the cell surface. The DNA is then endocytosed into the cell. Electroporation uses an electric field to create pores in the cell membrane, and the presumably the DNA enters through the pores. Generally, it is important to optimize the protocol for a given cell type. The concentration of DNA to be transfected, the concentration of the active agent for the transfection, and the time course of expression and selection of the transfected gene are all variables that must be determined for use and are within the skill of a person trained in the art.

Selection and Amplification of Recombinant Cells

Approximately one in $10^4$ cells in a transfection will stably integrate DNA, so a dominant selectable marker is used to permit isolation of stable transfectants. Appropriate selection conditions for the parental cell line are first determined and then applied to the transfected cells and allowed to grow under selection for approximately 10 doublings before individual colonies are chosen and expanded into cell lines. Several markers are commonly used for selection of mammalian cells. The selectable markers include adenosine deaminase(ADA), aminoglycoside phosphotransferase(neo, G418, APH), dihydrofolate reductase (DFR), hygromycin-B-phosptransferase(HPH), thymidine kinase (TK), and xanthine-guanine phosphoribosyltransferase (XGPRT, gpt).

Upon transfection with pHβAPr-1-neo-SKR, the cell population is exposed to environmental pressure (G418) sufficient to require the cell to produce more copies of the amplifiable gene, e.g. APH (aminoglycoside phosphotransferase), for survival. The cells are examined for the presence of the marker and those cells which have successfully incorporated the vector DNA with the marker gene will exhibit the marker phenotype. Thus when a cell is transfected with DNA containing the exogenous gene and a selectable marker, this enables the identification of those cells which have incorporated the DNA by selection of those cells that are able to survive drug treatment by expressing the requisite marker. The exogenous gene and the marker gene may be contained on a contiguous stretch of DNA or co-transfected on independent and separate stretches of DNA.

G418 is an antibiotic that blocks protein synthesis in mammalian cells by interfering with ribosomal function and is the basis for selection in the instant invention. G418 is an aminoglycoside, similar in structure to neomycin, gentamycin, and kanamycin. Expression of the bacterial APH gene (derived from the transposon tn5) in mammalian cells allows recombinant cells to survive by their ability to detoxify G418. (Southern, et. al., J. Mol. Appl. Gen. 1:327–341 (1982)).

Once the host cell line is transformed with the vector with the selectable gene and the gene coding for neurokinin A receptors, and the desired transformants are selected, they are screened for integration of the NKA receptor gene into the host chromosome or for expression of the receptor protein itself. Screening for expression of the integrated receptor gene can utilize standard immunological or biological assays. Once the transformants have been identified, expression of the receptor gene can be again amplified by subculturing the cells in the presence of the selecting agent, in constant or increasing concentrations, to yield cells producing higher levels of the receptor protein (1–500 femtomoles receptor per mg total protein in the assay). It should be noted that in the practice of this invention, transcription units may in general contain either cDNA or genomic DNA encoding neurokinin A receptors, a general marker such as neomycin resistance gene, and general transcriptional control sequences in operative association therewith.

Cells expressing neurokinin A receptors can be determined utilizing a radiolabeled-ligand binding assay. Essentially cell membranes from the cells to be determined are prepared from a cell lysate and a differential centrifugation of the membranes. The cell-membrane pellet is subsequently used in the binding assay. The binding assay consists of incubating the cell membranes in the presence of a radiolabeled ligand and determining the adsorption of the ligand into the membranes. Free versus bound ligand is generally separated by use of a filter binding assay. Specific binding is defined as the difference in binding between tubes containing no test compound and tubes containing unlabeled neurokinin A. Total membrane bound radioactivity is generally approximately 5% of that added to the tubes. Specific binding is generally 85–95% of total binding.

Biologically Active Receptors

One of the features of biologically active neurokinin A receptors includes the activation of a G protein, which inturn activates phospholipase C (PLC). PLC converts to phosphatidylinositol phosphate (PI) into inositol 1,4,5- triphosphate ($IP_3$) and diacyglycerol (DAG). $IP_3$ and DAG are believed to be intracellular signals of neurokinin A receptor activation.

EXPERIMENTAL PROCEDURE:

EXAMPLE 1

Construction of Cell Lines

B82 and transfected B82 cells are maintained in a medium containing 45% Dulbecco's modified Eagles's medium, 45% Ham's F-12 medium, 5% fetal bovine serum, 5% newborn calf serum, 100 U/ml of penicillin and 100 ug/ml of streptomycin. Cultures of transfected cells were periodically supplemented with 300 ug/ml of the selective antibiotic geneticin (G418; Gibco, Grand Island, N.Y.); . Cells were grown in Costar 75 $cm^2$ tissue culture flasks and incubated in a humidified atmosphere of 95% air and 5% $CO_2$.

Example 2

Introduction of the Neurokinin A Receptor cDNA into Mammalian Expression Vectors The bovine stomach cDNA clone, pSKR56S, was purified from a culture of its *E. coli* bacterial host utilizing standard alkaline lysis procedures. Several other suitable procedures for purifying plasmids are known to those skilled in the art.

The bovine cDNA in the plasmid was excised with suitable restriction endonucleases and ligated to the eukaryotic expression vector, pHβAPr-1-neo. For the construction of the expression plasmid pHβAPr-1-neo-SKR, the bovine cDNA in pSKR56S was first excised with the endonucleases XbaI and BamHI and ligated to the cloning vector pGEM3. This recombinant DNA was cloned and amplified, followed by HindIII and BamHI digestion to recover the cDNA insert, now flanked by a 5' HindIII end and a 3' BamHI end. These restriction sites facilitated the directional cloning of the bovine CDNA into the expression vector, pHβAPr-1-neo, which has a unique HindIII (5') and BamHI (3') site downstream from the promoter element for insertion and expression of heterologous genes. Cloning of the cDNA into the vector was accomplished using *E. coli* as the host and then purified from the host as a pure plasmid DNA preparation.

Example 3

Transfection of Mammalian Cells

The plasmid pHβAPr-1-neo-SKR, was transfected into the mammalian fibroblast L cell line, B82, by the calcium phosphate precipitation method. (Wigler et al., Cell 14, 727 (1978)). Essentially a precipitate containing $CaPO_4$ and DNA is formed by slowly mixing a HEPES-buffered saline solution with a solution containing $CaCl_2$ and DNA. The HEPES-buffered saline (HBS) was made up as a 10x concentrate containing 8.18% NaCl (w/v), 5.94% Hepes (w/v), 0.2% $Na_2HPO_4$ (w/v). For transfection the 10x solution was diluted to 2x with $dH_2O$ and the pH adjusted to 7.12 with 1N NaOH. This solution was filter sterilized before use. To prepare the DNA precipitate, 10–20 μg of supercoiled plasmid DNA was mixed with 31 μl of 2M $CaCl_2$ and brought to a final volume of 250 μl with sterile $dH_2O$. This mixture was then added dropwise to an equal volume of 2x HBS. This mixture (500 μl) was added to the culture medium of a 25 $cm^2$ flask which had been seeded with $10^4$ cells/$cm^2$ of B82 cells the day before transfection. The cells were immediately returned to the incubator and incubated for 3.5–4 hours. At the end of this incubation, a glycerol shock was usually carried out using 0.5 ml of 15% glycerol/HBS per flask for 1 min at 37° C. The cells were then rinsed with phosphate buffered saline and returned to the incubation medium as described above in a humidified atmosphere and 5% $CO_2$ for 48 hours prior to the addition of G-418 at 500 ug/ ml of medium. At this point the cells from each flask were transferred to two 100 mm petri dishes and the culture medium replaced with fresh medium that had been supplemented with 500 μg/ml of G-418. The medium was replenished after 4 days, and the cells were cultured in this supplemented medium until visible colonies formed. These colonies represent clonal cells which are resistant to G-418. The colonies, typically 1–3 mm in diameter, were harvested at random and expanded for subsequent screening procedures.

Example 4

Selection and Amplification of Integrated Vector

Neomycin resistant B82 colonies or clones were assayed for the presence of the protein product which was encoded by the foreign gene transfected into these cells. In the case of the instant clones, the bovine cDNA transfected into the B82 cells had previously been shown to encode for neurokinin A receptors.

The expression of the neurokinin A receptors in the B82 clones, categorized by the systematic name of SKLKB82#n (n of the systematic name designates different clonal isolates of the transfected cells). SKLKB82#n clones are stable with passage and culturing conditions for these cells are the same as that of the wild type B82 cells. The cell line SKLKB82#3 has been deposited with ATCC (ATCC CRL 10320).

The presence of the receptor protein in the B82 clones was established by a series of radiolabeled neurokinin A receptor binding assays. Several clones had observable levels of NKA receptors indicating that the bovine cDNA had been integrated into the genome of the B82 cells and was biologically and functionally being expressed.

Example 5

Characterization of Functional Neurokinin A Receptor in Trasfected B82 Cells by Receptor Binding Pellets of scraped cells of SKLKB82#n are homogenized with a Polytron (setting #6 for 15–30 sec) in 15 volumes of 50 mM TRIS-HCl buffer (pH 7.4, 4° C.) containing 120 mM NaCl and 5 mM KC1. The homogenate is centrifuged at 48,000×g for 10 min at 4° C. The pellet is resuspended (Polytron as above) in 15 volumes of 50 mM TRIS-HCl buffer (pH 7.4, 4° C.) containing 10 mM EDTA and 300 mM KCl and allowed to set on ice for 30 min. The suspension is centrifuged as above and the pellet is washed by resuspension and centrifugation two additional times in plain 50 mM TRIS-HCl buffer (pH 7.4, 4° C.). The final pellet is resuspended in a concentration of 1–10 mg/ml in incubation buffer (see below) and allowed to set at room temperature for approximately 15 minutes before use. The binding assay (Burcher, E., et al., J. Pharmacol. Exp. Ther., 236:819–831, 1986.) is carried out in duplicate or triplicate in 12 mm×75 mm polypropylene culture tubes in incubation buffer consisting of 50 mM TRIS-HCl (pH 7.4, room temperature) containing 0.1% bovine serum albumin, 2 mM $MnCl_2$, 40 ug/ml bacitracin, 4 ug/ml leupeptin, 4 ug/ml chymostatin, and 1 uM thiorphan. 0.25 nM ligand (400,000–500,000 CPM) diluted in incubation buffer is added to each tube in 50 ul. Test compound ($10^{-10}$M to $10^{-5}$ M) diluted in incubation buffer is added to appropriate tubes in 50 ul. The assay is started by the addition 250 ul (5 mg tissue) of well-mixed membrane suspension. The final incubation volume is 0.5 ml. The assay is carried out at room temperature for 2 hr. The incubation is quickly terminated by the addition of 3.5 ml of plain TRIS-HCl buffer (pH 7.4, 4° C.) and filtration under vacuum through GF/B filters that have been presoaked overnight in 0.5% BSA. The filters are rapidly washed with two 3.5 ml portions of the same buffer and transferred to 12 mm×75 mm polystyrene culture tubes for direct counting in a gamma scintillation counter. Specific binding is defined as the difference in binding between tubes containing no test compound and tubes containing 1 uM unlabeled neurokinin A. Total membrane bound radioactivity is generally approximately 5% of that added to the tubes. Specific binding is generally 85–95% of total binding.

Protein content of the crude membrane suspension can be determined (Lowry et al., J. Biol. Chem., 193:265, 1951) on an aliquot taken during the last tissue wash resuspension (plain 50 mM TRIS-HCl buffer).

Figure 3:
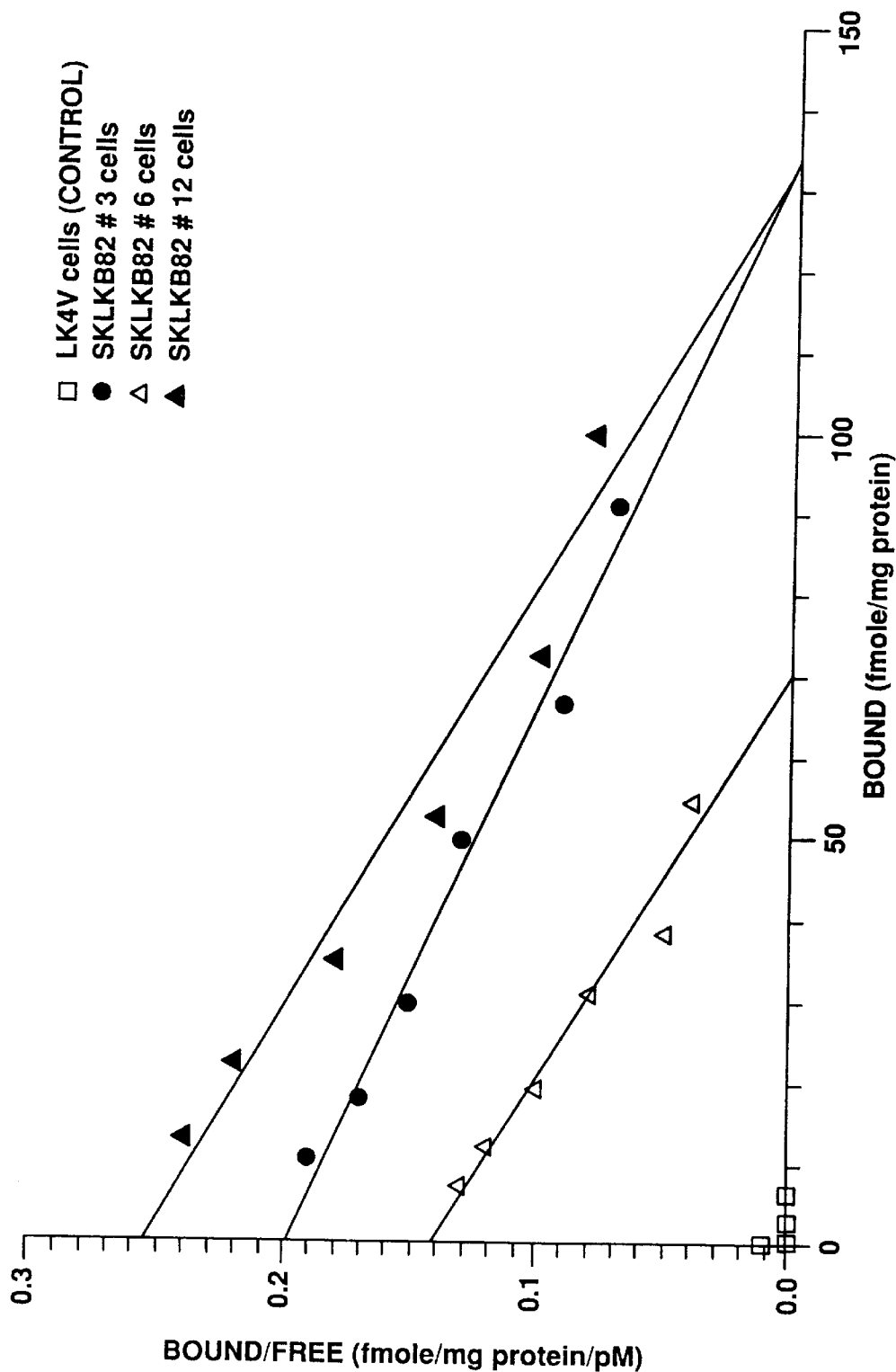
FIG. 3 Scatchard analaysis of [$^{125}$I]NKA saturation binding experiments was done for control cells and for three transfected cell lines with high levels of NKA receptor binding. There was no detectable binding in the control lines while all three cell lines transfected with pSKR56S cDNA exhibited substantial levels of receptor binding. $K_D$ values were 0.7 nM for SKLKB82#3, 0.5 nM for SKLKB82 #6, and 0.5 nM for SKLKB82 #12 (X-intercept=$B_{ma}X$; negative inverse of slope=$K_D$). In the same experiment, the hamster urinary bladder membranes were run as a standard control (Buck and Shatzer, Life Sciences 42, 2701, 1988) and yielded $B_{max}$ of 250 fmole/mg protein and $K_D$ of 0.8 nM. Therefore, the transfected NKA receptor cell lines contain a NKA receptor with similar affinity and a Bmax of 25–50% of tissue derived from hamster bladder.

Receptor binding experiments were utilized to identify and characterize B82 cells transfected with the Neurokenin A receptor expression plasmid pHβApr-1-neo-SKR. Results of these experiments are present in FIGS. 1–4.

INTERPRETATION OF RESULTS $IC_{50}$ is the molar concentration of compound that causes 50% inhibition of ligand binding(=$K_1$ is this particular assay; expressed as cumulative mean [±S.E.M.] of means from N separate experiments). Thereby from a Scatchard analysis of the data, the Bmax is obtained from the X-intercept and $K_D$ is obtained from the negative inverse slope of a Scatchard plot.

Example 6

$^3$H-Inositol-1-phosphate accumulation

The quantification of $IP_1$ was modified from Berridge et al. SKLKB82#3, a transfected cell line with high specific binding, was seeded into 1.6 cm diameter culture wells at 125,000/well. After a twenty four hour incubation at 37° C. under 95% humidified air/5% carbon dioxide, the media was removed and 0.5 ml Iscove's modified Dulbecco's medium (IMDM, Irvine Scientific) with 0.2 μM myo-[2,3H]inositol (20 Ci/mmol, NEN, Boston, Mass.) was added to the well. The culture was incubated for 22–24 hours under the same conditions. After this incubation, the cells were washed once with 1.0 ml of IMDM for ten minutes and incubated for ten minutes in 0.2 ml of incubation buffer (IMDM with 10 mM LiCl, 40 ug/ml bacitracin, 4 ug/ml leupeptin, and 4 ug/ml chymostatin). The agonists, NKA, SP (Peninsula Laboratories, Belmont, Calif.), and senktide (Bachem, Philadelphia, Pa.) were individually diluted in the incubation buffer before addition to the wells. For the antagonist assay, the incubation buffer also contained 10 uM L-659,877 (Merck Neurokinin A antagonist; A. T. McKnight, Regulatory Pep. 22, 127, 1988). The reaction was terminated in 60 minutes by aspirating the media and adding 0.5 ml methanol. The cells were scraped from the wells and placed into chloroform resistant tubes. A second aliquot of 0.5 ml methanol was used to collect the remaining cells. The cell suspensions were mixed with 1.0 ml chloroform and 0.5 ml double distilled water to obtain a two phase separation. After centrifugation at 4200g for 10 minutes, 0.9 ml aliquots of the upper phase were added to 2.0 ml of distilled water and mixed. This mixture was passed through poly prep columns (Bio-Rad Laboratories, Richmond, Calif.) which consisted of 2.0 ml slurry of ten percent anion exchange resin in formate form (AG1-X8, 100–200 mesh, Bio-Rad Laboratories, Richmond, Calif.). The columns were washed three times with 5.0 ml of distilled water and two times with 5.0 ml of 5 mM sodium tetraborate/60 mM sodium formate (Baker, Phillipsburg, N.J.). [3H]IP1 was eluted with 2.0 ml of 0.2M ammonium formate/0.1M formic acid (Mallinkrodt, St. Louis, Mo.). The eluate was mixed with nine ml of Aquamix (West Chem., San Diego, Calif.) and the radioactivity was counted.

$^3$H-Inositol-1-phosphate accumulation experiments were performed on B82 cells transfected with the Neurokinin A receptor expression plasmid pHβApr-1-neo-SKR. Results of this experiment are present in FIG. 5.

What is claimed is:

1. A cell line SKLKB82#n, for expressing neurokinin A receptors from an expression vector comprising the gene coding for the bovine neurokinin A receptor protein in operative association with transcriptional control sequences, wherein said cells express biologically active bovine neurokinin A receptors having both catalytic and effector activities for neurokinin A.

2. A method for amplifying cells of claim 1 which comprises culturing a cell line containing a selectable marker with a selective agent and culturing of the resultant cells giving rise to an increased level of gene expression; wherein Selectable markers are selected from, but not limited to, the genes for adenosine deaminase(ADA), aminoglycoside phosphotransferase (neo, G418, APH), dihydrofolate reductase (DFR), hygromycin-B-phosphotransferase(HPH), thymidine kinase (TK), and xanthine-guanine phosphoribosyltransferase (XGPRT, gpt).

3. A cell line according to claim 1, wherein said transcriptional control sequence is selected from the group consisting of the mouse mammary tumor virus long terminal repeat, rous sarcoma virus long terminal repeat, mouse metallothionein, human metallothionein, rat growth hormone transcriptional control sequence, and the human growth hormone transcriptional control sequence.

4. The method according to claim 1, wherein said mammalian cell lines are selected from existing mouse fibroblast cell lines.

5. A cell line according to claim 1, wherein said expression vector is pHβAPr-1-neo-SKR.

6. A cell line according to claim 1 that essentially comprises one of the elements of a kit for quantifying levels of neurokinin A.

7. A cell line according to claim 1 that essentially comprises one of the elements of a kit for finding compounds that effect binding to the neurokinin A receptor.

8. A cell line according to claim 1 that provides a source netrokinin A receptors.

9. A cell line of claim 1 having a nucleic acid sequence that is capable of hybridizing independently to each region of the plasmid pHβAPr-1-neo-SKR wherein said regions consist essentially of βAPr-1, the neomycin resistance gene, and the neurokinin A receptor gene.

10. A cell line of claim 1 having nucleic acid sequences which are degenerate as a result of the genetic code and wherein said nucleic acid sequences encode biologically functional neurokinin A receptors.

11. A cell line of claim 1 which produces neurokinin A receptors having reduced effector activities as determined by receptor binding.

12. A cell line of claim 1 which produces neurokinin A receptors having reduced catalytic activities as determined by phosphatidylinositol turnover activity.

13. A biologically pure culture of American Type Culture Collection [ATCC] deposit CRL 10320 [SKLB82#3].

* * * * *